United States Patent
Jackson et al.

(10) Patent No.: US 8,129,582 B2
(45) Date of Patent: Mar. 6, 2012

(54) ABSORBENT ARTICLE FEATURING A TEMPERATURE CHANGE MEMBER

(75) Inventors: David M. Jackson, Alpharetta, GA (US); Gabriel H. Adam, Alpharetta, GA (US); Andrew M. Long, Appleton, WI (US); Shirlee A. Weber, Neenah, WI (US); Davis Dang H. Nhan, Appleton, WI (US); Christopher P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 76 days.

(21) Appl. No.: 11/143,359

(22) Filed: Jun. 1, 2005

(65) Prior Publication Data

US 2006/0142714 A1      Jun. 29, 2006

Related U.S. Application Data

(63) Continuation-in-part of application No. 11/025,188, filed on Dec. 29, 2004.

(51) Int. Cl.
*A61F 13/15*      (2006.01)

(52) U.S. Cl. .................. 604/361; 604/364; 604/374

(58) Field of Classification Search .............. 604/361, 604/364–366, 374
See application file for complete search history.

(56) References Cited

U.S. PATENT DOCUMENTS

| | | | |
|---|---|---|---|
| 2,907,173 A | 10/1959 | Robbins | |
| 3,175,558 A | 3/1965 | Caillonette et al. | |
| 3,849,241 A | 11/1974 | Butin et al. | |
| 3,918,454 A | 11/1975 | Korodi et al. | |
| 4,029,100 A | 6/1977 | Karami | |
| 4,100,324 A | 7/1978 | Anderson et al. | |
| 4,231,370 A | 11/1980 | Mroz et al. | |
| 4,373,519 A | 2/1983 | Errede et al. | |
| 4,375,448 A | 3/1983 | Appel et al. | |
| 4,604,313 A | 8/1986 | McFarland et al. | |
| 4,655,757 A | 4/1987 | McFarland et al. | |
| 4,663,220 A | 5/1987 | Wisneski et al. | |
| 4,666,647 A | 5/1987 | Enloe et al. | |
| 4,673,403 A | 6/1987 | Lassen et al. | |
| 4,699,619 A | 10/1987 | Bernardin | |
| 4,704,116 A | 11/1987 | Enloe | |
| 4,761,258 A | 8/1988 | Enloe | |
| 4,773,905 A | 9/1988 | Molee et al. | |
| 4,834,733 A | 5/1989 | Huntoon et al. | |
| 4,940,464 A | 7/1990 | Van Gompel et al. | |
| 4,960,477 A | 10/1990 | Mesek | |
| 5,046,272 A | 9/1991 | Vogt et al. | |
| 5,104,116 A | 4/1992 | Pohjola | |
| 5,114,781 A | 5/1992 | Morman | |
| 5,116,662 A | 5/1992 | Morman | |
| 5,147,343 A | 9/1992 | Kellenberger | |
| 5,178,139 A | 1/1993 | Angelillo et al. | |
| 5,197,958 A | 3/1993 | Howell | |
| 5,213,881 A | 5/1993 | Timmons et al. | |

(Continued)

FOREIGN PATENT DOCUMENTS

| CA | 1 057 459 A | 7/1979 |
|---|---|---|
| CA | 2 074 649 A1 | 2/1993 |

(Continued)

*Primary Examiner* — Lynne Anderson
(74) *Attorney, Agent, or Firm* — Randall W. Fieldhack

(57) ABSTRACT

Disclosed is an absorbent article including a temperature change member. The temperature change member includes a matrix of fibers and temperature change material intermixed within the matrix of fibers.

27 Claims, 5 Drawing Sheets

U.S. PATENT DOCUMENTS

| | | | |
|---|---|---|---|
| 5,224,405 A | 7/1993 | Pohjola | |
| 5,226,992 A | 7/1993 | Morman | |
| 5,266,592 A | 11/1993 | Grub et al. | |
| 5,277,180 A | 1/1994 | Angelillo et al. | |
| 5,284,703 A | 2/1994 | Everhart et al. | |
| 5,286,770 A | 2/1994 | Bastioli et al. | |
| 5,348,750 A | 9/1994 | Greenberg | |
| 5,350,624 A | 9/1994 | Georger et al. | |
| 5,425,725 A | 6/1995 | Tanzer et al. | |
| 5,460,623 A | 10/1995 | Emenaker et al. | |
| 5,484,430 A | 1/1996 | Osborn, III | |
| 5,486,166 A | 1/1996 | Bishop et al. | |
| 5,486,410 A | 1/1996 | Groeger et al. | |
| 5,490,846 A | 2/1996 | Ellis et al. | |
| 5,494,622 A | 2/1996 | Heath et al. | |
| 5,536,511 A | 7/1996 | Yatka | |
| 5,575,785 A | 11/1996 | Gryskiewicz et al. | |
| 5,601,542 A | 2/1997 | Melius et al. | |
| 5,605,746 A | 2/1997 | Groeger et al. | |
| 5,607,760 A | 3/1997 | Roe | |
| 5,609,587 A | 3/1997 | Roe | |
| 5,645,542 A | 7/1997 | Anjur et al. | |
| 5,649,914 A | 7/1997 | Glaug et al. | |
| 5,658,268 A | 8/1997 | Johns et al. | |
| 5,662,728 A | 9/1997 | Groeger | |
| 5,681,289 A | 10/1997 | Wilcox et al. | |
| 5,681,298 A | 10/1997 | Brunner et al. | |
| 5,702,376 A | 12/1997 | Glaug et al. | |
| 5,702,377 A | 12/1997 | Collier, IV et al. | |
| 5,766,389 A | 6/1998 | Brandon et al. | |
| 5,769,835 A | 6/1998 | Fell et al. | |
| 5,797,892 A | 8/1998 | Glaug et al. | |
| 5,814,035 A | 9/1998 | Gryskiewicz et al. | |
| 5,861,440 A | 1/1999 | Gohla et al. | |
| 5,863,288 A | 1/1999 | Baker | |
| 5,883,028 A | 3/1999 | Morman et al. | |
| 5,885,264 A | 3/1999 | Matsushita | |
| 5,900,109 A | 5/1999 | Sanders et al. | |
| 5,913,851 A | 6/1999 | Gryskiewicz et al. | |
| 5,921,974 A | 7/1999 | Kikuchi | |
| 5,935,118 A | 8/1999 | Gryskiewicz et al. | |
| 5,964,743 A | 10/1999 | Abuto et al. | |
| 5,994,614 A | 11/1999 | Wada et al. | |
| 6,126,648 A | 10/2000 | Keck et al. | |
| 6,159,591 A | 12/2000 | Beihoffer et al. | |
| 6,163,961 A | 12/2000 | McMeekin | |
| 6,180,847 B1 | 1/2001 | Ahr et al. | |
| 6,221,460 B1 | 4/2001 | Weber et al. | |
| 6,231,557 B1 | 5/2001 | Krautkramer et al. | |
| 6,245,410 B1 | 6/2001 | Hähnle et al. | |
| 6,306,412 B1 | 10/2001 | Crotty et al. | |
| 6,319,599 B1 | 11/2001 | Buckley | |
| 6,330,735 B1 | 12/2001 | Hahn et al. | |
| 6,362,389 B1 | 3/2002 | McDowall et al. | |
| 6,414,035 B1 | 7/2002 | Vargas Munita et al. | |
| 6,437,212 B1 | 8/2002 | La Fortune | |
| 6,461,086 B1 | 10/2002 | Milanowski et al. | |
| 6,541,025 B1 | 4/2003 | Kershman et al. | |
| 6,552,245 B1 | 4/2003 | Roessler et al. | |
| 6,582,413 B2 | 6/2003 | Krautkramer et al. | |
| 6,620,791 B1 | 9/2003 | Cooper et al. | |
| 6,627,786 B2 | 9/2003 | Roe et al. | |
| 6,642,427 B2 | 11/2003 | Roe et al. | |
| 6,645,190 B1 | 11/2003 | Olson et al. | |
| 6,657,100 B1 | 12/2003 | Underhill et al. | |
| 6,667,424 B1 * | 12/2003 | Hamilton et al. | 604/375 |
| 6,794,557 B1 | 9/2004 | Klemp et al. | |
| 6,867,343 B2 | 3/2005 | La Fortune | |
| 7,002,055 B2 | 2/2006 | Long et al. | |
| 7,147,629 B2 | 12/2006 | Ishikawa et al. | |
| 7,632,978 B2 * | 12/2009 | Olson et al. | 604/361 |
| 2003/0130636 A1 | 7/2003 | Brock et al. | |
| 2003/0147941 A1 | 8/2003 | Koenig et al. | |
| 2003/0199845 A1 | 10/2003 | Roe et al. | |
| 2004/0015143 A1 | 1/2004 | Underhill et al. | |
| 2004/0030310 A1 | 2/2004 | Roe et al. | |
| 2004/0082928 A1 | 4/2004 | Pesce et al. | |
| 2004/0185093 A1 | 9/2004 | Szymczak | |
| 2004/0254549 A1 | 12/2004 | Olson et al. | |
| 2004/0254550 A1 | 12/2004 | Huang et al. | |
| 2005/0070867 A1 | 3/2005 | Beruda et al. | |
| 2005/0096623 A1 | 5/2005 | Nhan et al. | |
| 2005/0137085 A1 | 6/2005 | Zhang et al. | |
| 2005/0148961 A1 | 7/2005 | Sosalla et al. | |
| 2006/0004336 A1 | 1/2006 | Zhang et al. | |
| 2006/0005919 A1 | 1/2006 | Schewe et al. | |
| 2006/0069363 A1 * | 3/2006 | Weber et al. | 604/361 |
| 2006/0142713 A1 | 6/2006 | Long et al. | |
| 2006/0142715 A1 * | 6/2006 | Long et al. | 604/364 |
| 2006/0142716 A1 * | 6/2006 | Long et al. | 604/364 |
| 2006/0247588 A1 | 11/2006 | Olson et al. | |
| 2006/0293632 A1 * | 12/2006 | Long et al. | 604/361 |

FOREIGN PATENT DOCUMENTS

| | | |
|---|---|---|
| CA | 1 315 488 C | 4/1993 |
| CA | 2 208 888 A1 | 6/1996 |
| CA | 2 208 891 A1 | 6/1996 |
| CA | 2 312 840 A1 | 6/1999 |
| CA | 2 183 238 C | 2/2001 |
| CA | 2 391 936 A1 | 2/2001 |
| CA | 2 228 130 C | 12/2001 |
| CA | 2 228 043 C | 1/2002 |
| CA | 2 441 135 A1 | 10/2002 |
| CA | 2 467 968 A1 | 6/2003 |
| CA | 2 461 275 A1 | 9/2004 |
| DE | 36 08 114 A1 | 9/1987 |
| DE | 197 45 878 C1 | 12/1998 |
| EP | 0 203 715 A2 | 12/1986 |
| EP | 0 339 461 A1 | 11/1989 |
| EP | 0 217 032 B1 | 2/1992 |
| EP | 0 538 535 A1 | 4/1993 |
| EP | 0 704 195 A2 | 4/1996 |
| JP | 2001-031520 A | 2/2001 |
| JP | 2003-020568 A | 1/2003 |
| WO | WO 00/37009 A2 | 6/2000 |
| WO | WO 01/88245 A2 | 11/2001 |
| WO | WO 03/051254 A2 | 6/2003 |
| WO | WO 03/051258 A1 | 6/2003 |
| WO | WO 03/053481 A1 | 7/2003 |
| WO | WO 03/057109 A1 | 7/2003 |
| WO | WO 03/057122 A1 | 7/2003 |
| WO | WO 2004/022115 A1 | 3/2004 |
| WO | WO 2005/004771 A1 | 1/2005 |

* cited by examiner

US 8,129,582 B2

ABSORBENT ARTICLE FEATURING A TEMPERATURE CHANGE MEMBER

This application is a continuation-in-part of U.S. patent application Ser. No. 11/025,188 filed Dec. 29, 2004, and entitled "Absorbent Article Featuring a Temperature Change Member". The entirety of application Ser. No. 11/025,188 is hereby incorporated by reference.

BACKGROUND OF THE INVENTION

The present invention relates to absorbent articles that include a temperature change member. More specifically, the invention relates to an absorbent article such as training pants that provides the wearer with a noticeable temperature change sensation upon urination.

Absorbent articles such as disposable diapers and training pants are useful to absorb and contain body wastes. These products have developed to the extent that urine is quickly drawn and retained away from the wearer's skin so that the wearer remains relatively dry and comfortable. Although this improved performance enhances wearer dryness and comfort, it can reduce the wearer's ability to notice or recognize when urination occurs, especially if the wearer's attention is distracted by an activity. This is not conducive to toilet training because an important step in the early stages of toilet training is the ability to recognize when urination occurs. In an attempt to enhance a child's recognition of when urination occurs, training pants have been designed with temperature change members that provide a temperature change sensation upon urination.

Unfortunately, in certain circumstances, such temperature change members may not be completely satisfactory. For example, in aspects where a particulate temperature change material is utilized in the temperature change member, shake-out of the temperature change material can occur during processing, packaging, or even during use thereby reducing the effectiveness of the temperature change member. Moreover, depending on the configuration of the temperature change member, it may be difficult to incorporate into an article with a high-speed manufacturing process.

Thus, there is a need for an absorbent article with a temperature change member that is capable of suitably retaining the temperature change material within the temperature change member during manufacture, packaging and during use. Further, there is a need for an absorbent article with a temperature change member that may be easily processed and incorporated into an article by a high-speed manufacturing process. Still further there is a need for such temperature change members that provide these advantages and yet effectively provides a temperature change sensation to the wearer during use.

SUMMARY OF THE INVENTION

In one aspect, the present invention is directed to an absorbent article including a liquid impermeable outercover, an absorbent body disposed on the outercover and a temperature change member disposed with the absorbent body. The temperature change member includes a temperature change composite including a matrix of fibers and temperature change material intermixed within the matrix of fibers where the temperature change member provides the article with a temperature change of at least 5 degrees C., as determined by the temperature change test described herein.

In another aspect, the present invention is directed to an absorbent article including a liquid impermeable outercover, an absorbent body disposed on the outercover, and a temperature change member disposed with the absorbent body. The temperature change member includes a temperature change composite including a matrix of absorbent fibers and temperature change material intermixed within the matrix of absorbent fibers. In addition, the temperature change member provides the article with a surface temperature change when wet of from 5 to 15 degrees C., as determined by the temperature change test described herein.

In yet another aspect, the present invention is directed to an absorbent article including a liquid impermeable outercover, an absorbent body disposed on the outercover and a temperature change member disposed with the absorbent body. The temperature change member includes a temperature change composite including a matrix of adhesive fibers and temperature change material intermixed within the matrix of adhesive fibers. In addition, the temperature change member provides the article with a surface temperature change when wet of from 5 to 15 degrees C., as determined by the temperature change test described herein.

In still yet another aspect the present invention is directed to an absorbent article including a liquid impermeable outercover, an absorbent body disposed on the outercover and a temperature change member disposed with the absorbent body. The temperature change member includes a temperature change composite including a coform matrix of fibers including polymer fibers and absorbent fibers and temperature change material intermixed within the coform matrix of fibers. In addition, the temperature change member provides the article with a surface temperature change when wet of from 5 to 15 degrees C., as determined by the temperature change test described herein.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

Definitions

Figure 1:
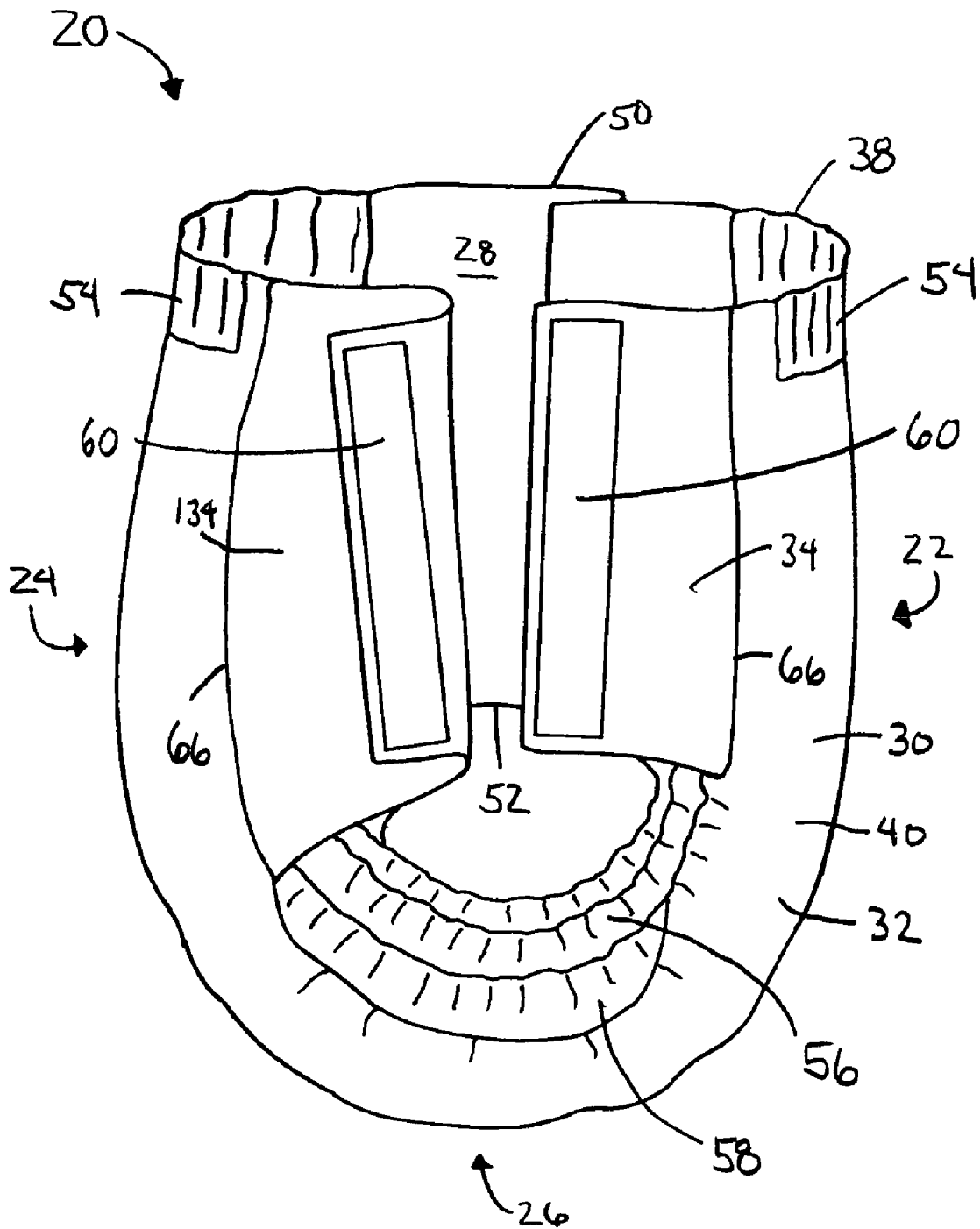
FIG. 1 representatively illustrates a side view of a pair of training pants with a mechanical fastening system of the pants shown fastened on one side of the training pants and unfastened on the other side of the training pants.

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 25 percent (to 125 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Stretchable" means that a material can be stretched, without breaking, by at least 25 percent (to 125 percent of its initial (unstretched) length) in at least one direction. Elastic materials and extensible materials are each stretchable materials.

"superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Referring now to the drawings and in particular to FIG. 1, an absorbent article of the present invention is representatively illustrated in the form of children's toilet training pants and is indicated in its entirety by the reference numeral 20. The pants 20 include a temperature change member 70 that is adapted to create a distinct temperature change sensation to the wearer upon urination, which can enhance a wearer's ability to recognize when urination is occurring. The pants 20 may or may not be disposable, which refers to articles that are intended to be discarded after a limited period of use instead of being laundered or otherwise conditioned for reuse. It should also be understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10,1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent that they are consistent (i.e., not in conflict) herewith. In addition, absorbent articles including a temperature change member are described in U.S. Pat. No. 5,681,298 to Brunner et al., the disclosure of which is incorporated herein by reference to the extent that it is consistent (i.e., not in conflict) herewith.

Figure 2:
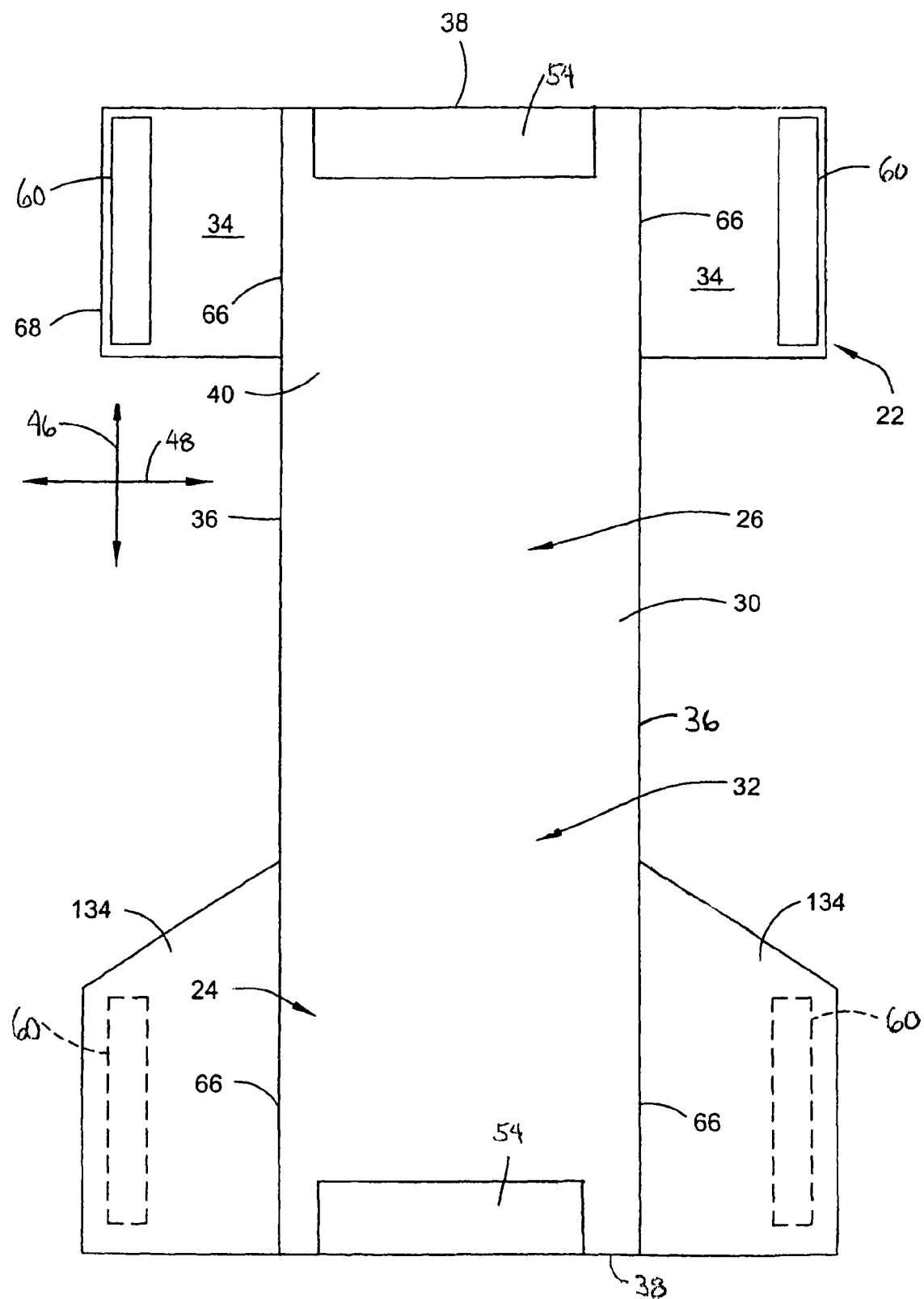
FIG. 2 representatively illustrates a plan view of the training pants of FIG. 1 in an unfastened, stretched and laid flat condition, and showing the surface of the training pants that faces away from the wearer.
Figure 3:
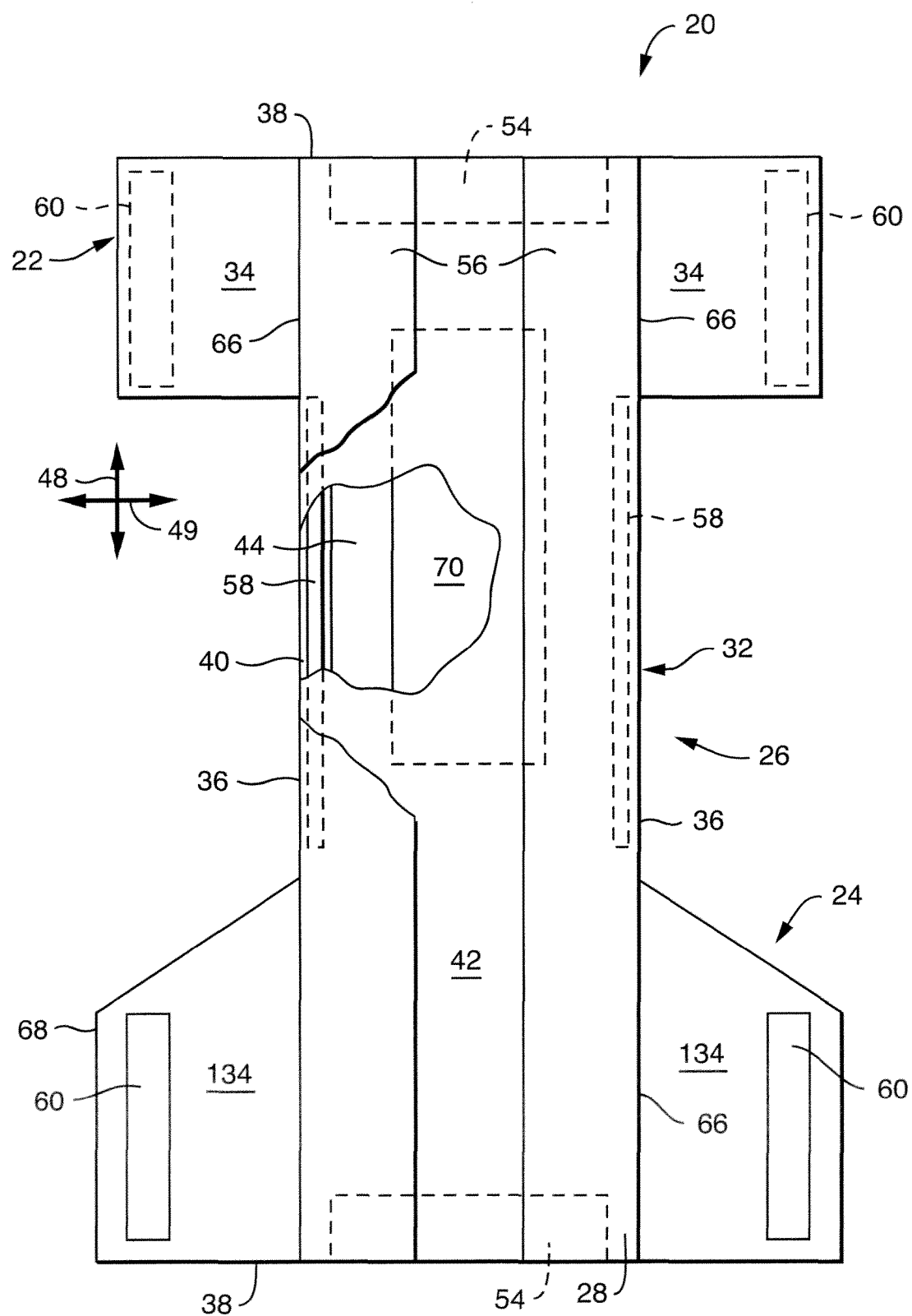
FIG. 3 representatively illustrates a plan view similar to FIG. 2, but showing the surface of the training pants that faces the wearer when worn, and with portions cut away to show underlying features.

The pair of training pants 20 is illustrated in. FIG. 1 in a partially fastened condition. The pants 20 define a longitudinal direction 46 and a lateral direction 48 perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 includes those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use to be disposed toward the wearer, and an outer surface 30 opposite the inner surface. With additional reference to FIGS. 2 and 3, the pair of training pants 20 has a pair of laterally opposite side edges 36 and a pair of longitudinally opposite waist edges 38 (broadly, longitudinal ends).

The illustrated pants 20 can include an absorbent assembly, generally indicated at 32. For example, in the aspect of FIGS. 1-3, the training pants 20 include a generally rectangular central absorbent assembly 32 and side panels 34, 134 formed separately from and secured to the central absorbent assembly. The side panels 34, 134 can be bonded along seams 66 to the absorbent assembly 32 in the respective front and back waist regions 22 and 24 of the pants 20. More particularly, the front side panels 34 can be permanently bonded to and extend laterally outward from the absorbent assembly 32 at the front waist region 22, and the back side panels 134 can be permanently bonded to and extend laterally from the absorbent assembly 32 at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus include the portions of the training pants 20 that are positioned on the hips of the wearer. The front and back side panels 34 and 134 can be permanently bonded together to form the three-dimensional configuration of the pants 20, or be releasably connected with one another such as by a fastening system 60 of the illustrated aspects.

Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference in their entirety to the extent they are consistent (i.e., not in conflict) herewith. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the side panels 34, 134 may include elastic material or stretchable but inelastic materials.

The absorbent assembly 32 is illustrated in FIGS. 1-3 as having a rectangular shape. However, it is contemplated that the absorbent assembly 32 may have other shapes (e.g., hour-glass, T-shaped, I-shaped, and the like) without departing from the scope of this invention. It is also understood that the side panels 34, 134 may alternatively be formed integrally with the absorbent assembly 32 without departing from the scope of this invention. In such a configuration, the side panels 34 and 134 and the absorbent assembly would include at least some common materials, such as the bodyside liner 42, outercover 40, other materials and/or combinations thereof.

The absorbent assembly 32 includes an outercover 40 and a bodyside liner 42 (FIG. 3) in a superposed relation therewith. The liner 42 can be suitably joined to the outercover 40 along at least a portion of the longitudinal ends of the pants 20. The liner 42 can be suitably adapted, i.e., positioned relative to the other components of the pants 20, to contact the wearer's skin during wear of the pants. The absorbent assembly 32 also includes an absorbent body 44 (FIG. 3) disposed between the outercover 40 and the bodyside liner 42 for absorbing liquid body exudates. The liner 42 can be suitably joined to the outercover 40 along at least a portion of the longitudinal ends of the pants 20. The bodyside liner 42 and the outercover 40 can, for example, be attached to each other by adhesive, ultrasonic bonding, thermal bonding or by other suitable attachment techniques known in the art. Moreover, at least a portion of the absorbent body 44 can optionally be attached to the bodyside liner 42 and/or the outercover 40 utilizing the methods described above.

As mentioned above, the front and back side panels 34 and 134 can be releasably connected with one another such as by the fastening system 60 of the illustrated aspect. With the training pants 20 in the fastened position as partially illustrated in FIG. 1, the front and back waist regions are connected together to define the three-dimensional pants configuration having a waist opening 50 and a pair of leg openings 52. The waist edges 38 (e.g., longitudinal ends) of the training pants 20 are configured to encircle the waist of the wearer to define the waist opening 50 (FIG. 1) of the pants.

The fastening system 60 may include any refastenable fasteners suitable for absorbent articles, such as adhesive fasteners, cohesive fasteners, mechanical fasteners, or the like. In one aspect of the invention, the fastening system includes mechanical fastening elements for improved performance. Suitable mechanical fastening elements can be provided by interlocking geometric-shaped materials, such as hooks, loops, bulbs, mushrooms, arrowheads, balls on stems, male and female mating components, buckles, snaps, or the like. For example, fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The pants 20 may further include a pair of containment flaps 56 for inhibiting the lateral flow of body exudates. As illustrated in FIG. 3, the containment flaps 56 can be operatively attached to the pants 20 in any suitable manner as is well known in the art. In particular, suitable constructions and arrangements for the containment flaps 56 are generally well known to those skilled in the art and are described in U.S. Pat. No. 4,704,116 issued Nov. 3, 1987 to Enloe, which is incorporated herein by reference to the extent that it is consistent (i.e., not in conflict) herewith.

To further enhance containment and/or absorption of body exudates, the training pants 20 may include waist elastic members 54 in the front and/or back waist regions 22 and 24 of the pants 20. Likewise, the pants 20 may include leg elastic members 58, as are known to those skilled in the art. The waist elastic members 54 and the leg elastic members 58 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

The outercover 40 may suitably include a material that is substantially liquid impermeable. The outercover 40 may be provided by a single layer of liquid impermeable material, or more suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outercover 40 may include a woven or non-woven fibrous web layer that has been totally or partially constructed or treated to impart the desired levels of liquid impermeability to selected regions that are adjacent or proximate the absorbent body.

The outercover 40 may also be stretchable, and in some aspects it may be elastomeric. For example, such an outercover material can include a 0.3 osy polypropylene spunbond that is necked 60 percent in the lateral direction 40 and creped 60 percent in the longitudinal direction 48, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outercover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent body 44. A suitable liquid permeable bodyside liner 42 is a nonwoven polyethylene/polypropylene bicomponent web having a basis weight of about 27 gsm; the web may be spunbonded or a bonded carded web. Optionally, the bodyside liner 42 may be treated with a surfactant to increase the wettability of the liner material.

Alternatively, the bodyside liner 42 may also be stretchable, and in some aspects it may be elastomeric. For instance, the liner 42 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued Apr. 22, 2003, to Roessler et al., which is incorporated by reference herein to the extent that it is consistent (i.e., not in conflict) herewith.

An absorbent body 44 may be disposed on the outercover 40, for example, between the outercover 40 and the bodyside liner 42. The outercover 40 and the bodyside liner 42 can be joined together by any suitable means such as adhesives, ultrasonic bonds, thermal bonds, or the like. The absorbent body 44 can be in a variety of shapes and configurations as are known in the art, such as rectangular, hourglass shaped, I-shaped, and the like. Further, at least a portion of the absorbent body 44 can optionally be attached to the bodyside liner 42 and/or the outercover 40 utilizing the methods described above.

The absorbent body 44 is suitably compressible, conformable and capable of absorbing and retaining liquid body exudates released by the wearer. For example, the absorbent assembly can include a matrix of absorbent fibers, and more suitably cellulosic fluff, such as wood pulp fluff, and superabsorbent particles. One suitable pulp fluff is identified with the trade designation CR1654, commercially available from Bowater, Inc. of Greenville, S.C., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The absorbent body 44 can have a density within the range of about 0.10 to about 0.5 grams per cubic centimeter and may be wrapped or encompassed by a suitable tissue or nonwoven wrap for maintaining the integrity and/or the shape of the absorbent assembly.

In one aspect, the absorbent body 44 may be stretchable so as not to inhibit the stretchability of other components to which the absorbent body may be adhered, such as the outercover 40 and/or the bodyside liner 42. For example, the absorbent body may include materials disclosed in U.S. Pat. Nos. 5,964,743, 5,645,542, 6,231,557, 6,362,389, and international patent application WO 03/051254,the disclosure of each of which is incorporated by reference herein.

In some aspects, a surge management layer (not shown) may be included in the pants 20. The surge management layer may be positioned in the pants 20 in a variety of locations as shown in the art. For example, the surge management layer can be proximate the absorbent body 44, for example between the absorbent body 44 and the bodyside liner 42, and attached to one or more components of the pants 20 by methods known in the art, such as by adhesive, ultrasonic or thermal bonding. In addition, the surge management layer may be positioned in the pants 20 relative to the temperature change member 70 in a variety of ways. For instance, the surge management layer may be disposed toward the liner 42 relative to the temperature change member 70, or the surge management layer may be disposed toward the absorbent body 44 relative to the temperature change member 70.

A surge management layer helps to decelerate and diffuse surges or gushes of liquid that may be rapidly introduced into the absorbent body 44. Desirably, the surge management layer can rapidly accept and temporarily hold the liquid prior to releasing the liquid into the storage or retention portions of the absorbent body 44. Examples of suitable surge management layers are described in U.S. Pat. Nos. 5,486,166 and 5,490,846, the contents of which are incorporated herein by reference to the extent that they are consistent (i.e., not in conflict) herewith.

Figure 4:
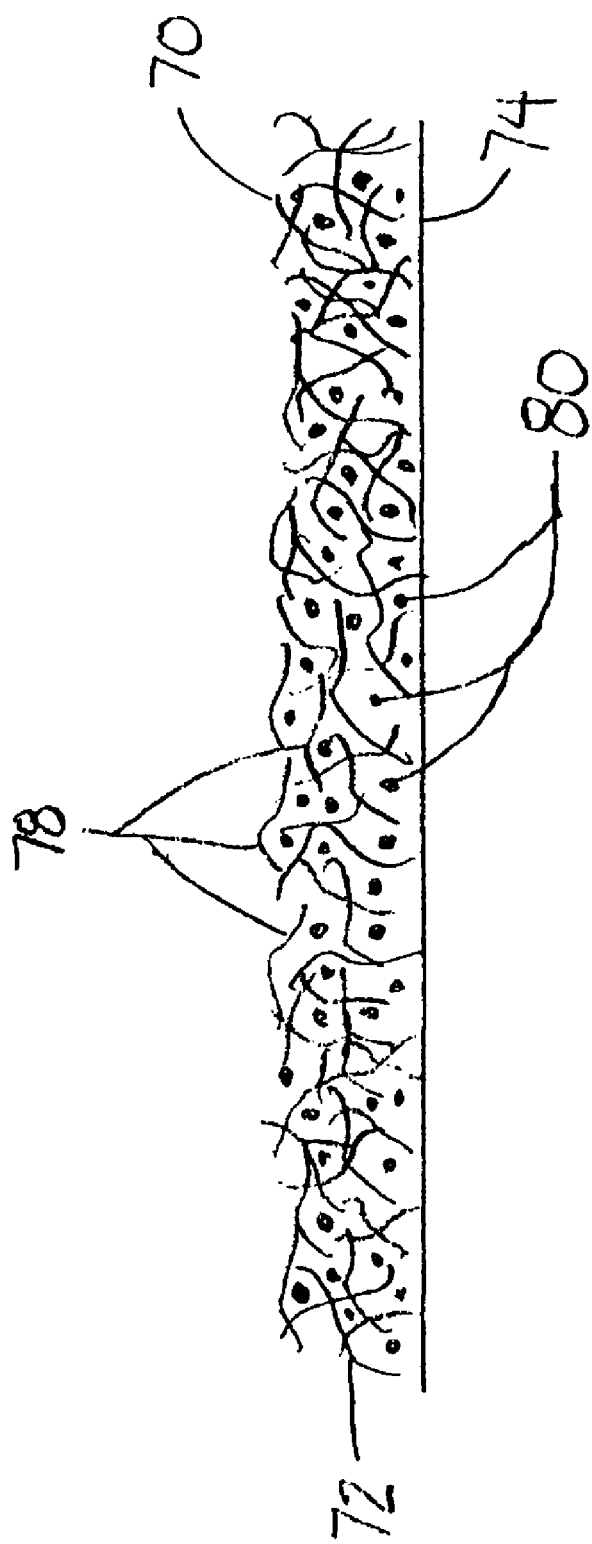
FIG. 4 representatively illustrates a section view of a particular aspect of the temperature change member of the present invention.
Figure 5:
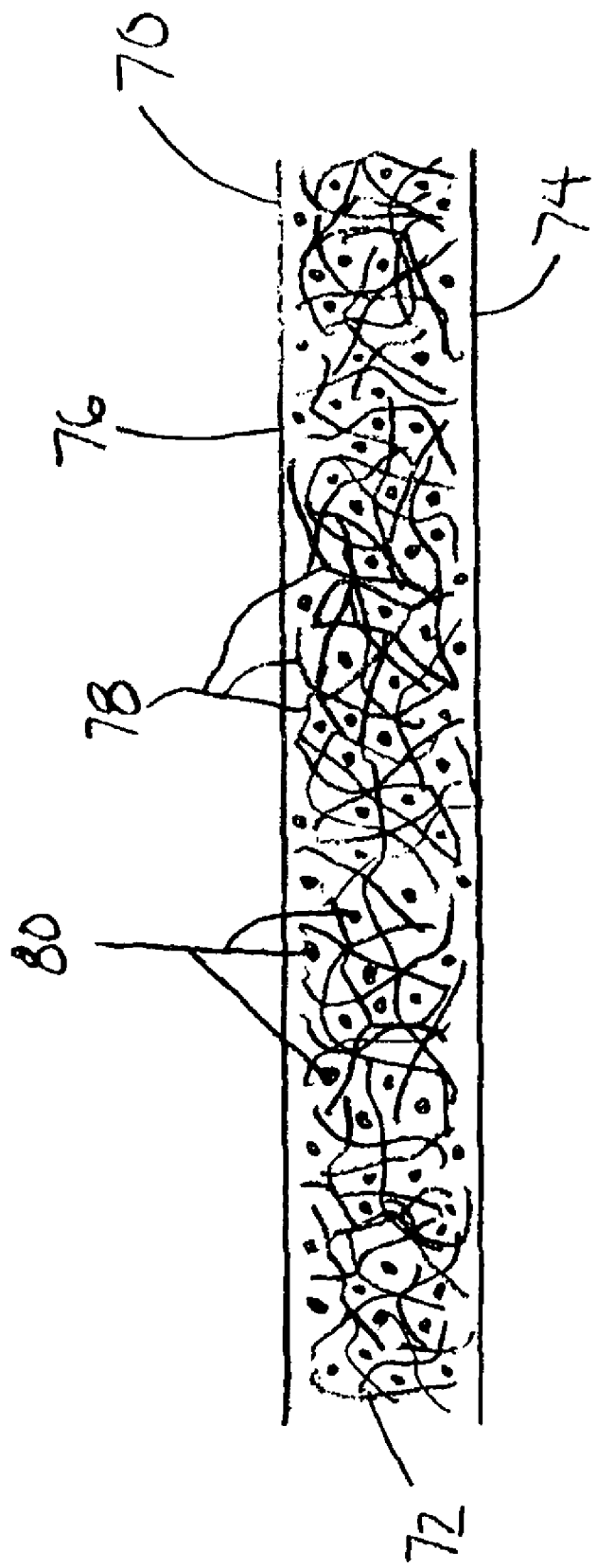
FIG. 5 representatively illustrates a section view of another aspect of the temperature change member of the present invention.

As mentioned above, in the various aspects of the absorbent article of the present invention, the pants 20 can also include a temperature change member 70 (FIG. 3). The temperature change member 70 can include a temperature change composite 72 and optionally a first carrier layer 74 in a superposed relationship with temperature change composite 72 (FIGS. 4 and 5). The temperature change member 70 can also optionally include a second carrier layer 76 where the first carrier layer 74 and the second carrier layer 76 sandwich the temperature change composite 72 (FIG. 5).

As representatively illustrated in FIGS. 4 and 5, the temperature change composite 72 can include a matrix of fibers 78 and temperature change material 80 intermixed within the matrix of fibers 78. The matrix of fibers 78 may be substantially continuous or discrete and discontinuous. In addition, the matrix of fibers 78 of the temperature change composite 72 may be provided by a variety of different fibers as are known in the art. For example, the matrix of fibers 78 can include adhesive fibers, absorbent fibers, binders (including binder fibers), polymer fibers, and the like or combinations thereof. As such, the temperature change material 80 may be suitably entrapped within the matrix 78 to limit material shake-out or loss during manufacture and/or wear of the pants 20.

In particular, in aspects where the matrix of fibers 78 includes adhesive fibers, the fibers may be provided by a hot-melt adhesive. Such an adhesive generally comprises one or more polymers to provide cohesive strength, a resin or analogous material, perhaps waxes, plasticizers or other materials to modify viscosity, and/or other additives including, but not limited to, antioxidants or other stabilizers.

As an example, a suitable hot-melt adhesive may contain from about 15 to about 50 weight percent cohesive strength polymer or polymers; from about 30 to about 65 weight percent resin or other tackifier or tackifiers; from more than zero to about 30 weight percent plasticizer or other viscosity modifier; and optionally less than about 1 weight percent stabilizer or other additive. It should be understood that other hot-melt adhesive formulations comprising different weight percentages of these components are possible.

An example of a suitable adhesive for use in providing the matrix of fibers 78 are hot-melt adhesives available from H.B. Fuller Adhesives of Saint Paul, Minn. under the designation HL8151-XZP. In particular, this adhesive is a hydrophilic adhesive which promotes the rapid wettability of the temperature change member 70 resulting in faster temperature change. Alternatively, it is contemplated that the adhesive can be a hydrophobic adhesive without departing from the scope of the present invention.

Further examples of suitable adhesive compositions are those made by National Starch and Chemical Co. of Bridgewater, N.J., under the designations 34-5610 and 34-447A and those available from Bostik-Findley in Milwaukee, Wis. under the designations HX 4207-01,HX 2773-01,H2525A and H2800.Moreover, suitable adhesives are further described in U.S. patent application Ser. No. 10/699,193 filed Oct. 31, 2003 in the name of Sawyer, et al., the disclosure of which is hereby incorporated by reference to the extent that it is consistent (i.e., not in conflict) herewith. It is also contemplated that alternative adhesives may be used without departing from the scope of this invention.

The matrix of fibers 78 may be produced by adhesive fibers in a variety of adhesive application processes as are known in the art. For example, adhesive may be meltblown onto a foraminous surface, such as a screen, or onto a substrate such as the first carrier layer 74 that can be placed onto the foraminous surface. In particular, a suitable adhesive applicator system may be used to apply the adhesive in the form of discrete fibers or filaments. For instance, the resulting matrix of fibers 78 can have an adhesive fiber diameter in the range of about 5 microns to about 200 microns, and more suitably in the range of about 7 microns to about 50 microns. Suitable adhesive applicator systems are known in the art and are available from Nordson Corporation of Duluth, Ga., U.S.A., or ITW Dynatec Co. of Hendersonville, Tenn., U.S.A.

In one aspect, adhesive fibers may have a basis weight in the range of about 1 to about 150 grams per square meter (gsm), and more suitably in the range of about 50 to about 100 gsm to form the matrix of fibers 78. Similarly, the temperature change material 80 may have a basis weight in the range of about 500 to about 2000 grams per square meter (gsm), and more suitably in the range of about 1000 to about 1500 gsm to form the matrix of fibers 78. In another aspect, the amount of adhesive used in forming the temperature change composite is suitably less than or equal to about 20 percent by weight of the amount of temperature change material used in forming the temperature change composite 72, more suitably less than or equal to about 10 percent by weight of the amount of temperature change material used in forming the temperature change composite 72, and still more suitably in the range of about 5 to about 10 percent by weight. In a particular aspect, the temperature change composite can be 95 gsm adhesive and 1400 gsm temperature change material 80.

The temperature change material 80 can be intermixed with the adhesive fibers providing the matrix of fibers 78 by being fed into and entrained in a stream of adhesive to form a blended mixture of adhesive fibers and temperature change material 80 that can be applied to a substrate, such as the first carrier layer 74. Optionally, the second carrier layer 76 can overlay the temperature change composite 72 and be secured thereto by the adhesive in the matrix of fibers 78.

In such an aspect, the temperature change member 70 can optionally be subjected to further processing. For example, as will be described in greater detail below, a compressive force may be applied to the temperature change member 70 to facilitate strengthening of the bonds between the matrix of fibers 78 and the temperature change composite 72 as well as between the matrix of fibers 78 and any carrier layers that may optionally be present 74 and/or 76. The compression may also reduce the thickness, or caliper of the temperature change member 70 such that it may be more discreetly included in the pants 20.

Alternatively, the matrix of fibers 78 of the temperature change composite 72 can include absorbent fibers. Suitable absorbent fibers can include natural absorbent fibers such as cellulosic fibers (i.e., wood pulp fibers) or cotton fibers, synthetic absorbent fibers such as rayon or cellulose acetate or combinations thereof. In particular, the absorbent fibers can be a mixed bleached southern softwood and hardwood Kraft pulp designated as CR1654 available from Bowater Inc. of Greenville, S.C. U.S.A. Other suitable absorbent fibers can include NB 416,a bleached southern softwood Kraft pulp available from Weyerhaeuser Co. of Federal Way, Wash. U.S.A.; CR 1654, a bleached southern softwood Kraft pulp available from Bowater, Incorporated, of Greenville, S.C. U.S.A.; SULPHATATE HJ, a chemically modified hardwood pulp available from Rayonier Inc. of Jesup, Ga. U.S.A. and NF 405, a chemically treated bleached southern softwood Kraft pulp available from Weyerhaeuser Co.

Optionally, in such an aspect, the matrix of fibers 78 can further include binder material. For example, the binder material can suitably be a thermoplastic binder material. Such binder materials can soften when exposed to heat and can substantially returns to their original condition when cooled to room temperature. Such thermoplastic binder materials, when in the softened state, constrain or entrap the fibers and other materials proximate the binder to stabilize the temperature change composite 72. Binder materials can be provided in powder or fiber form. Examples of suitable binder materials for use with the present invention can be those having low melting temperatures such as polyethylene glycol (PEG) or paraffin wax, both of which are available from Alrich of Saint Louis, Mo.

In such an aspect, the matrix of fibers 78 may be provided by absorbent fibers by forming the matrix on a forming surface of a conventional air-forming device. Such air-forming devices are well known to those skilled in the art for use in forming fibrous webs. For example, reference is made to U.S. Pat. Nos. 4,666,647, issued May 19, 1987, to Enloe et al., and U.S. Pat. No. 4,761,258 issued Aug. 2, 1988, to Enloe, the disclosures of which are incorporated herein by reference to the extent that they are consistent (i.e., not in conflict) herewith. In such devices, fibrous material is introduced and may be mixed with other material such as the temperature change material 80 prior to collecting on the forming surface. A pneumatic flow mechanism, such as a vacuum suction system, draws the air-entrained fiber stream within the air-forming device toward the forming surface so that air passes through the foraminous surface while the fibers and other air-entrained material collect on the forming surface.

Thus, a matrix of absorbent fibers 78 and temperature change material 80 intermixed with the matrix can be collected on the forming surface to form the temperature change composite 72. Optionally, an air permeable substrate can be laid upon the forming surface to collect the temperature change composite 72 and provide a first carrier layer 74. Further a second carrier layer 76 can be placed upon the temperature change composite following the formation of the temperature change composite in the air-forming device to increase the integrity of the temperature change member 70.

The temperature change member 70 (with or without the first and second carrier layers 74 and 76) may be further processed, such as by passing the temperature change member through a nip defined by opposed rolls in order to compress it down to a uniform thickness. Following compression in this manner, the temperature change member 70 can define a density of between 0.20 grams per $cm^3$ to 0.55 grams per $cm^3$, particularly a density of between 0.25 grams per $cm^3$ to 0.45 grams per $cm^3$ and still more particularly, a density of 0.35 grams per $cm^3$. Alternatively, other densification methods may be utilized as are well known to those skilled in the art. Densities within these ranges are believed to allow provide a flexible temperature change member 70 that retains the temperature change material 80 within the matrix of fibers 78 and that has desirable integrity. Moreover, such densities are not so high as to crush or otherwise impair the temperature change material 80 thereby reducing its efficacy. In addition, in aspects where the temperature change composite 72 includes binder material, the temperature change member 70 can optionally be subjected to heat activation such as by heat calendar rolls or a through air heating device.

The temperature change composite 72 including absorbent fibers as described above can be from 5 to 50 percent by weight absorbent fibers, and from 50 to 95 percent by weight temperature change material. Alternatively, the temperature change composite 72 can be from 20 to 40 percent by weight absorbent fibers, and from 60 to 80 percent by weight temperature change material 80. Optionally, the composite 72 may include between 1 and 15 percent by weight binder fibers. In a particular aspect, the temperature change composite 72 can be 70 percent by weight temperature change material 80 and 30 percent by weight absorbent fibers and define a density of 0.35 grams per $cm^3$.

In yet another alternative the matrix of fibers 78 may be provided by a coform composite including polymer fibers and absorbent fibers. Coform materials and coforming processes are known in the art and by way of example are described in U.S. Pat. No. 4,100,324 to Anderson, et al.; U.S. Pat. No. 5,284,703 to Everhart, et al.; and U.S. Pat. No. 5,350,624 to Georger, et al.; each of which are hereby incorporated by reference to the extent that they are consistent (i.e., not in conflict) herewith.

In a particular aspect, the matrix of fibers 78 may be provided by a coform composite that can be a blend of meltblown polymer fibers and cellulosic fibers. Various suitable materials may be used to provide the meltblown fibers such as a polyolefin material. Alternatively, the polymer fibers may be stretch polymer fibers, such as those provided by a copolymer resin. For instance, Vistamaxx® elastic olefin copolymer resin designated PLTD-1819 available from ExxonMobil Corporation of Houston, Tex. or KRATON G-2755 available from Kraton Polymers of Houston, Tex. may be used to provide stretchable polymer fibers for the matrix of fibers 78. Other suitable polymeric materials or combinations thereof may alternatively be utilized as are known in the art.

Further, various absorbent cellulose fibers may be utilized, such as NF 405, a chemically treated bleached southern softwood Kraft pulp available from Weyerhaeuser Co. of Federal Way, Wash. U.S.A.; NB 416, a bleached southern softwood Kraft pulp available from Weyerhaeuser Co.; CR-0056, a fully debonded softwood pulp available from Bowater Inc. of Greenville S.C., Golden Isles 4822 debonded softwood pulp available from Koch Cellulose of Brunswick, Ga., U.S.A.; and SULPHATATE HJ, a chemically modified hardwood pulp available from Rayonier Inc. of Jesup, Ga. U.S.A.

The polymer fibers and the meltblown fibers may be coformed to provide the matrix of fibers 78 by providing a stream of absorbent fibers and a stream of extruded molten polymeric fibers. Further, to provide the temperature change composite 72, a stream of temperature change material 80 can also be provided. These streams can be merged into a single stream and collected on a forming surface such as a forming belt or forming drum to form the temperature change composite 72 of the temperature change member 70. Optionally, a forming layer, such as first carrier layer 74, can be placed on the forming surface and used to collect the materials included in the temperature change composite 72.

The stream of absorbent fibers may be provided by feeding a pulp sheet into a fiberizer, hammermill, or similar device as are known in the art. Suitable fiberizers are available from Hollingsworth of Greenville, S.C. and are described in U.S. Pat. No. 4,375,448 issued Mar. 1, 1983 to Appel et al. The stream of polymer fibers may be provided by meltblowing a copolymer resin or other polymer. In particular, the melt temperature for a copolymer resin such as Vistamaxx® PLTD 1810 can be from 450 degrees F. (232 degrees C.) to 540 degrees F. (282 degrees C.) to improve the entrainment of the temperature change material in the matrix. As mentioned above, suitable techniques for producing nonwoven fibrous webs, which include meltblown fibers are described in the previously incorporated U.S. Pat. Nos. 4,100,324 and 5,350,624. The meltblowing techniques can be readily adjusted in accordance with conventional know-how to provide turbulent flows that can operatively intermix the fibers and the temperature change material 80. For example, the primary air pressure may be set at 5 psi and the meltblown nozzles may be 0.020 inch spinneret hole nozzles. The techniques can also be readily adjusted in accordance with conventional knowledge to provide the desired weight percentages of the various materials in the temperature change composite 72.

The stream of temperature change material 80 may be pneumatically provided or gravity fed. A suitable method and apparatus for delivering material in an airstream is described in U.S. Pat. No. 4,604,313 issued Aug. 5, 1986 to McFarland et al.; the disclosure of which is incorporated by reference herein to the extent that it is consistent (i.e., not in conflict) herewith. The coform material may also include other materials, such as superabsorbent materials.

In one aspect, the temperature change composite 72 provided by a coform composite as described above may be from 5 to 15 percent by weight meltblown polymer fibers, 10 to 50 percent by weight absorbent fibers and 40 to 80 percent by weight temperature change material. In a particular aspect, the temperature change composite 72 can be 8 percent by weight meltblown polymer fibers, 14 percent by weight absorbent fibers, 78 percent by weight temperature change material and define a basis weight of 1340 gsm.

As mentioned above, the temperature change member 70 can optionally include a first carrier layer 74 (FIGS. 4 and 5) in superposed relationship with the temperature change composite 72. Further, the temperature change member 70 can optionally include a first carrier layer 74 and a second carrier layer 76 (FIG. 5) where the first carrier layer and the second carrier layer 76 sandwich the temperature change composite 72. The first and second carrier layers 74 and 76 may be provided by separate webs of material, or alternatively can be provided by a single web of material that is folded in half about the temperature change composite 72.

In certain aspects, the carrier layers 74 and 76 can be liquid permeable or liquid impermeable. For instance, one carrier layer, such as the first carrier layer 74 may be liquid impermeable and the other carrier layer, (i.e., the second carrier layer 76 can be liquid permeable. In such an aspect, the first carrier layer 74 can be disposed toward the exterior surface 32 and the second carrier layer 76 can be disposed toward the interior surface 30. As such, liquid insults may pass through the second carrier layer 76 to activate the temperature change material, and the first carrier layer 74 can slow the flow of the liquid insult from leaving the temperature change member 70 thus maximizing the temperature change that can be felt by the wearer. Alternatively, the first carrier layer 74 can be liquid permeable, and in aspects with a second carrier layer 76, both carrier layers 74 and 76 may be liquid permeable. Such carrier layers 74 and 76 can further improve the integrity of the temperature change member 70 for improved processability and can also aid in retaining the temperature change material within the member 70.

Suitable liquid permeable materials for the carrier layers 74 and 76 include tissue layers, nonwoven layers, or combinations thereof. In particular, materials described as suitable for use as the bodyside liner 42 may also be suitable for a liquid permeable carrier layer 74 and 76. Accordingly, a liquid permeable carrier layer 74 and 76 can also be stretchable. Likewise, materials described as suitable for use as the outercover 40 may be suitable for use as a liquid impermeable carrier layer 74 and 76. Accordingly, a liquid impermeable carrier layer 74 and 76 can also be stretchable.

The temperature change material 80 of the various aspects of the present invention can include a substance that provides a temperature change when placed near the wearer and contacted with urine. The temperature change can be either an absorption or release of heat that is noticeable to the wearer. Absorption of heat by the temperature change material 80 will provide the wearer with a cool sensation, while a release of heat by the substance will provide the wearer with a warm sensation. Reference is made to aforementioned U.S. patent application Ser. No. 10/462,166, in the name of Olson, et al., incorporated by reference herein, for additional information regarding the mechanism by which the temperature change sensation is accomplished. Suitably, the temperature change material 80 can be provided in particulate form for ease of processing in the described aspects.

The temperature change material 80 can be homogeneously intermixed within said matrix of fibers 78. Alternatively, the temperature change material 80 can define a distribution gradient within the thickness of the temperature change composite 72. For example, the temperature change material 80 may be intermixed within the matrix of fibers 78 in greater amounts toward the interior surface 30 of the pants. Alternatively, the temperature change material 80 may be intermixed within the matrix of fibers 78 in greater amounts toward the exterior surface 30 of the pants.

The temperature change material 80 is responsive to contact with an aqueous solution such as urine to either absorb or release heat. The mechanism by which this is accomplished is dissolution of the substance in the aqueous solution, swelling of the substance in the aqueous solution, or reaction of the substance in the aqueous solution. For example, the temperature change material may include particles that have a substantial energy difference between a dissolved state and a crystalline state so that energy in the form of heat is absorbed or released to the environment upon contact with urine, or the temperature change material may release or absorb energy during swelling or reacting in an aqueous solution.

While a wide variety of substances may result in a temperature change when contacted with an aqueous solution, the selection of a particular temperature change material 80, the determination of the amount to be used and the location of the substance should be based in part on the desired temperature change. Specifically, the temperature change member 70 may suitably provide the training pants 10 with a temperature change (i.e., cooler or warmer) when wet of at least about 5 degrees C., more suitably about 10 degrees C., still more suitably about 15 degrees C. Alternatively, the temperature change member 70 can provide the pant 20 with a surface temperature change when wet of from 5 degrees C. to 15 degrees C. Surface temperature changes within this range are believed to be identifiable to some extent by children of toilet training age. More suitably the temperature change member 70 can provide the pant 20 with a surface temperature change when wet of from 5 degrees C. to 10 degrees C.

Thus, in a particular aspect, where the temperature change material is endothermic, a drop in the temperature of the product when insulted can be from about 37 degrees C. to about 25 degrees C., and further to about 22 degrees C. for improved effectiveness, particularly with a preoccupied wearer (i.e., a playing child). The temperature change can suitably last for at least 10 minutes, and more suitably for approximately 15 minutes.

By way of example, Xylitol particles may be selected to provide a cooling sensation as Xylitol particles absorb heat when dissolved in an aqueous solution. Other suitable temperature change materials that absorb heat during dissolution include salt hydrates, such as sodium acetate ($H_2O$), sodium carbonate ($10H_2O$), sodium sulfate ($10H_2O$), sodium thiosulfate ($5H_2O$), and sodium phosphate ($10H_2O$); anhydrous salts such as ammonium nitrate, potassium nitrate, ammonium chloride, potassium chloride, and sodium nitrate; organic compounds such as urea or the like.

The temperature change material 80 may also include those substances that absorb or release heat during swelling. By way of illustration, one suitable temperature change material that releases heat during swelling is a lightly cross-linked partially neutralized polyacrylic acid. Other temperature change material 80 that releases heat during dissolution includes aluminum chloride, aluminum sulfate, potassium aluminum sulfate, or the like.

The temperature change material 80 can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued to Greenberg, and U.S. Pat. No. 5,266,592 issued to Grub et al.

Thus, as described above, the temperature change member 70 can include a matrix of fibers 72 and the temperature change material 80, such as Xylitol particles, intermixed within the matrix of fibers 72. Once wet by urination, the Xylitol dissolves, creating an endothermic response, thereby signaling to the wearer that urination has occurred.

The temperature change member 70 is disposed within the training pants 20 so that, upon urination, liquid makes contact with the temperature change material 80. For example, the temperature change member 70 can be disposed with the absorbent body 44, for example intermediate the outercover 40 and liner 42. In particular, the temperature change member 70 may be attached to the absorbent body 44 and disposed toward the interior surface of the pants 20. Alternatively, the temperature change member 70 may be attached to the liner 42 adjacent the absorbent body 44. In still yet another alternative, the temperature change member 70 can be disposed within a gap between potions of the absorbent body 44 and attached, for example, to the outercover 40. Such an aspect is described in U.S. patent application Ser. No. 10/955,534 filed Sep. 29, 2004, in the name of Weber, et al., the disclosure of which is incorporated by reference to the extent that it is consistent (i.e., not in conflict) herewith.

As can be readily appreciated, the temperature change member 70 can be of various shapes and sizes. For example, the temperature change member 70 can be rectangular and can have a width in the lateral direction 48 of from 2.5 cm to 10 cm and a length in the longitudinal direction 46 of from 2.5 cm to 25 cm. In one aspect the temperature change member 70 can measure about 8 cm by about 10 cm. Alternatively, the temperature change member 70 can be oval in shape, circular, triangular, or the like. In yet another alternative, the temperature change member 70 can be generally be provided in strips that extend in the lateral 48 or longitudinal direction 46 and that can be separated by a gap of about 2.5 cm.

Further, the temperature change member 70 can suitably contain various amounts of the temperature change material 80 as described above. Further, it will be understood by those of skill in the art that the training pants 20 of the present invention could include more than one temperature change member 70.

Therefore, as can be readily appreciated, the pants 20 of the various aspects of the present invention provide a temperature change member 70 that effectively signals urination to the wearer and may be readily processed in a high-speed converting process with a limited amount of temperature change material 80 shake-out or loss.

A suitable procedure for determining the temperature change when wet of a product containing a temperature change material is described below in the temperature change test as follows. The test should be conducted in an environment having a stable temperature of 21 degrees C. to 22 degrees C. and a stable humidity of about 50 percent. The product to be tested is prepared by removing any elastic side panels and cutting all other elastics to permit the product to lay as flat as possible. The product is positioned in a Plexiglas cradle to simulate the configuration of the product in actual use. The center of the product is placed in the deepest portion of the cradle.

A liquid dispensing nozzle operatively connected to a liquid dispensing pump is positioned to dispense saline onto the inner surface of the product. The tip of the nozzle should be located 1 cm away from the inner surface and 10 cm forward of the center of the product, along the product's longitudinal axis. The pump is activated to dispense 90 ml of a stabilized isotonic 0.9 percent saline at a rate of 15 ml/sec. The saline is certified blood bank saline available from The Baxter Healthcare Corporation, Scientific Products Division, McGraw Park, Ill., and is at a temperature of 37° C.

The surface temperature of the product at the location of the temperature change member is measured using a standard thermometer or temperature sensing thermistors connected to a digital display or recording device. The surface temperature 30 seconds after the saline is dispensed is recorded as the test temperature. A reference temperature is obtained by performing this test on a portion of the product not including the temperature change material or on a similar product without the temperature change material. The surface temperature change when wet for the product is the difference between the test temperature and the reference temperature.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article comprising:

A liquid impermeable outercover;

a liquid permeable bodyside liner in a superposed relationship with the outercover;

An absorbent body disposed on said outercover, the absorbent body including absorbent body fibers; and A temperature change member disposed with said absorbent body, said temperature change member comprising a temperature change composite and a first carrier layer in superposed relationship with said temperature change composite, the temperature change composite comprising a matrix of temperature change member fibers and temperature change material intermixed within said matrix of temperature change member fibers, wherein the temperature change member fibers are of a type different from the absorbent body fibers, and wherein said temperature change member provides said article with a temperature change of at least 5 degrees C., as determined by the temperature change test described herein.

2. The absorbent article of claim 1 wherein said matrix of temperature change member fibers comprises adhesive fibers.

3. The absorbent article of claim 2 wherein said adhesive fibers are provided by a hot melt adhesive.

4. The absorbent article of claim 1 wherein said matrix of temperature change member fibers comprises absorbent fibers.

5. The absorbent article of claim 4 wherein said temperature change composite comprises from 20 percent to 40 percent by weight said absorbent fibers and from 60 percent to 80 percent by weight temperature change material.

6. The absorbent article of claim 4 wherein said absorbent fibers are cellulosic fibers.

7. The absorbent article of claim 4 wherein said matrix of temperature change member fibers further comprises binder material.

8. The absorbent article of claim 4 wherein said temperature change member defines a density of between 0.25 grams per cm$^3$ to 0.45 grams per cm$^3$.

9. The absorbent article of claim 1 wherein said matrix of temperature change member fibers is provided by a coform composite comprising polymer fibers and absorbent fibers.

10. The absorbent article of claim 9 wherein said polymer fibers are meltblown polymer fibers.

11. The absorbent article of claim 10 wherein said polymer fibers are stretch polymer fibers.

12. The absorbent article of claim 9 wherein said absorbent fibers are cellulosic fibers.

13. The absorbent article of claim 9 wherein said temperature change composite comprises from 5 percent to 15 percent by weight said polymer fibers, from 10 percent to 50 percent by weight said absorbent fibers, and from 40 percent to 80 percent by weight said temperature change material.

14. The absorbent article of claim 1 wherein said carrier layer is stretchable.

15. The absorbent article of claim 1 wherein said carrier layer is liquid impermeable.

16. The absorbent article of claim 1 wherein said carrier layer is liquid permeable.

17. The absorbent article of claim 1 wherein said temperature change member further comprises a second carrier layer and wherein said first carrier layer and said second carrier layer sandwich said temperature change composite.

18. The absorbent article of claim 17 wherein said first and second carrier layers are liquid permeable.

19. The absorbent article of claim 17 wherein one of said first and second carrier layers are liquid impermeable.

20. The absorbent article of claim 1 wherein said temperature change material is an endothermic material.

21. The absorbent article of claim 1 wherein said temperature change material is an exothermic material.

22. The absorbent article of claim 1 wherein said temperature change material is homogeneously intermixed within said matrix of temperature change member fibers.

23. The absorbent article of claim 1, wherein the temperature change member provides the article with a surface temperature change when wet of at least 10 degrees C., as determined by the temperature change test described herein.

24. The absorbent article of claim 1, wherein the temperature change member provides said article with a surface temperature change when wet of from 5 to 15 degrees C., as determined by the temperature change test described herein.

25. An absorbent article comprising:

A liquid impermeable outercover;

a liquid permeable bodyside liner in a superposed relationship with the outercover;

An absorbent body disposed on said outercover, the absorbent body including absorbent body fibers; and A temperature change member disposed with said absorbent body, said temperature change member comprising a temperature change composite and a first carrier layer in superposed relationship with said temperature change composite, the temperature change composite comprising a matrix of temperature change member absorbent fibers and temperature change material intermixed within said matrix of temperature change member absorbent fibers, wherein the temperature change member absorbent fibers are of a type different from the absorbent body fibers, wherein the first carrier layer separates the temperature change member absorbent fibers from the absorbent body fibers, and wherein said temperature change member provides said article with a surface temperature change when wet of from 5 to 15 degrees C., as determined by the temperature change test described herein.

26. An absorbent article comprising:

A liquid impermeable outercover;

a liquid permeable bodyside liner in a superposed relationship with the outercover;

An absorbent body disposed on said outercover, the absorbent body including absorbent body fibers; and A temperature change member disposed with said absorbent body, said temperature change member comprising a temperature change composite and a first carrier layer in superposed relationship with said temperature change composite, the temperature change composite comprising a matrix of temperature change member adhesive fibers and temperature change material intermixed within said matrix of temperature change member adhesive fibers, wherein the temperature change member adhesive fibers are of a type different from the absorbent body fibers, and wherein said temperature change member provides said article with a surface temperature change when wet of from 5 to 15 degrees C., as determined by the temperature change test described herein.

27. An absorbent article comprising:

A liquid impermeable outercover;

An absorbent body disposed on said outercover, the absorbent body including absorbent body fibers; and A temperature change member disposed with said absorbent body, said temperature change member comprising a temperature change composite comprising a coform matrix of temperature change member fibers comprising polymer fibers and absorbent fibers and temperature change material intermixed within said coform matrix of temperature change member fibers, wherein the first carrier layer separates the temperature change member fibers from the absorbent body fibers, wherein said temperature change member provides said article with a surface temperature change when wet of from 5 to 15 degrees C., as determined by the temperature change test described herein.

* * * * *